(12) United States Patent
Flores (10) Patent No.: US 6,976,987 B2
(45) Date of Patent: *Dec. 20, 2005

(54) DUAL-PROFILE STEERABLE CATHETER

(75) Inventor: Jesse Flores, Perris, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 133 days.

This patent is subject to a terminal disclaimer.

(21) Appl. No.: 10/611,371

(22) Filed: Jun. 30, 2003

(65) Prior Publication Data

US 2004/0059326 A1    Mar. 25, 2004

Related U.S. Application Data

(63) Continuation of application No. 09/848,103, filed on May 2, 2001, now Pat. No. 6,610,058.

(51) Int. Cl.[7] .............................................. A61B 18/18
(52) U.S. Cl. ...................... 606/41; 604/95.04; 600/585
(58) Field of Search ......................... 604/95.04, 95.05; 606/41; 607/122; 600/585

(56) References Cited

U.S. PATENT DOCUMENTS

| | | |
|---|---|---|
| 3,521,620 A | 7/1970 | Cook |
| 4,886,067 A | 12/1989 | Palermo |
| 4,921,482 A | 5/1990 | Hammerslag et al. |
| 4,979,510 A | 12/1990 | Franz et al. |
| 4,998,916 A | 3/1991 | Hammerslag et al. |
| 5,037,391 A | 8/1991 | Hammerslag et al. |
| 5,108,368 A | 4/1992 | Hammerslag et al. |
| 5,125,896 A | 6/1992 | Hojeibane |
| 5,195,968 A | 3/1993 | Lundquist et al. |
| 5,228,441 A | 7/1993 | Lundquist |
| 5,254,088 A | 10/1993 | Lundquist et al. |
| 5,273,535 A * | 12/1993 | Edwards et al. ......... 604/95.01 |
| 5,315,996 A | 5/1994 | Lundquist |
| 5,318,525 A | 6/1994 | West et al. |
| 5,318,526 A | 6/1994 | Cohen |
| 5,322,064 A | 6/1994 | Lundquist |
| 5,327,905 A | 7/1994 | Avitall |

(Continued)

FOREIGN PATENT DOCUMENTS

EP    0 774 232    5/1997

(Continued)

OTHER PUBLICATIONS

Grafton A. Smith, M.D. and Edwin L. Brackney, M.D., "Preliminary Report on a New Method of Intestinal Intubation with the Aid of a Flexible Stylet with Controllable Tip," Dept. of Surgery, University of Minnesota Medical School, vol. 27, #6, Jun. 1950, pp. 817-821.

*Primary Examiner*—Michael Peffley
(74) *Attorney, Agent, or Firm*—Faegre & Benson LLP (57) ABSTRACT

A catheter includes a steering mechanism for manipulating the distal end of the catheter to obtain a plurality of deflection profiles. The steering mechanism comprises two steering tendons. The first steering tendon is attached to the distal-end region and the second steering tendon is attached to the distal-end region at a location proximal the attachment point of the first steering tendon. The steering tendons may be located approximately angularly aligned, thus causing the deflection profiles to be unidirectional. Alternatively, the steering tendons may be angularly separated from each other, thus causing the deflection profiles to be bidirectional. The steering tendons are attached so that moving the first steering tendon in a proximal direction causes the distal-end region to deflect in a tight loop, whereas moving the second steering tendon in a proximal direction causes the distal-end region to deflect in a U-shape.

20 Claims, 5 Drawing Sheets

U.S. PATENT DOCUMENTS

| | | | |
|---|---|---|---|
| 5,329,923 A | 7/1994 | Lundquist | |
| 5,334,145 A | 8/1994 | Lundquist et al. | |
| 5,336,182 A | 8/1994 | Lundquist et al. | |
| 5,358,478 A | 10/1994 | Thompson et al. | |
| 5,358,479 A | 10/1994 | Wilson | |
| 5,363,861 A | 11/1994 | Edwards et al. | |
| 5,368,564 A | 11/1994 | Savage | |
| 5,372,587 A | 12/1994 | Hammerslag et al. | |
| 5,383,852 A | 1/1995 | Stevens-Wright | |
| 5,383,923 A | 1/1995 | Webster, Jr. | |
| 5,385,148 A | 1/1995 | Lesh et al. | |
| 5,395,327 A | 3/1995 | Lundquist et al. | |
| 5,397,304 A * | 3/1995 | Truckai | 604/528 |
| 5,478,330 A | 12/1995 | Imran et al. | |
| 5,487,757 A | 1/1996 | Truckai et al. | |
| 5,489,270 A | 2/1996 | van Erp | |
| 5,496,260 A | 3/1996 | Krauter et al. | |
| 5,507,725 A | 4/1996 | Savage et al. | |
| 5,531,686 A | 7/1996 | Lundquist et al. | |
| 5,545,200 A | 8/1996 | West et al. | |
| 5,603,697 A | 2/1997 | Grundy et al. | |
| 5,642,736 A | 7/1997 | Avitall | |
| 5,674,197 A | 10/1997 | van Muiden et al. | |
| 5,687,723 A | 11/1997 | Avitall | |
| 5,715,817 A * | 2/1998 | Stevens-Wright et al. | 600/373 |
| 5,755,760 A | 5/1998 | Maguire et al. | |
| 5,782,828 A | 7/1998 | Chen et al. | |
| 5,797,842 A | 8/1998 | Pumares et al. | |
| 5,810,802 A | 9/1998 | Panescu et al. | |
| 5,855,552 A | 1/1999 | Houser et al. | |
| 5,855,560 A | 1/1999 | Idaomi et al. | |
| 5,865,800 A | 2/1999 | Mirarchi et al. | |
| 5,882,333 A | 3/1999 | Schaer et al. | |
| 5,891,088 A | 4/1999 | Thompson et al. | |
| 5,893,885 A | 4/1999 | Webster, Jr. | |
| 5,916,147 A | 6/1999 | Boury | |
| 5,928,191 A | 7/1999 | Houser et al. | |
| 5,944,689 A | 8/1999 | Houser et al. | |
| 5,984,907 A | 11/1999 | McGee et al. | |
| 6,022,343 A | 2/2000 | Johnson et al. | |
| 6,033,378 A | 3/2000 | Lundquist et al. | |
| 6,059,778 A | 5/2000 | Sherman | |
| 6,063,077 A | 5/2000 | Schaer | |
| 6,096,036 A | 8/2000 | Bowe et al. | |
| 6,142,994 A | 11/2000 | Swanson et al. | |
| 6,163,716 A | 12/2000 | Edwards et al. | |
| 6,183,463 B1 | 2/2001 | Webster et al. | |
| 6,208,881 B1 | 3/2001 | Champeau | |

FOREIGN PATENT DOCUMENTS

| | | |
|---|---|---|
| EP | 1 046 406 | 10/2000 |
| WO | WO 96/40344 | 12/1996 |

* cited by examiner

DUAL-PROFILE STEERABLE CATHETER

RELATED APPLICATIONS

This is a continuation of application Ser. No. 09/848,103, filed May 2, 2001, which is now U.S. Pat. No. 6,610,058, the entire contents of which are hereby incorporated by reference.

BACKGROUND OF THE INVENTION

The invention relates generally to catheters, and more particularly to a catheter having a steerable dual-profile distal-end region.

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery or vein to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate electrophysiological ("EP") catheter system.

One such EP catheter system, as disclosed in U.S. Pat. Nos. 6,059,778 and 6,096,036, includes a plurality of spaced apart band electrodes located at the distal end of the catheter and arranged in a linear array. The band electrodes are positioned proximal heart tissue. RF energy is applied through the electrodes to the heart tissue to produce a series of long linear lesions similar to those produced by the Maze procedure. The catheters currently used for this procedure are typically flexible at the distal end, and the profile at the distal end is adjustable. However, when using such catheters, it is often difficult to conform the distal-end profile to some of the irregular topographies of the interior cavities of the heart. In other instances, it is difficult for a multi-electrode catheter that is designed to produce long linear lesions to access and ablate tissue in regions that require short linear lesions, such as the so-called isthmus region that runs from the tricuspid annulus to the eustachian ridge. Ablation of tissue in this region, and other regions non-conducive to the placement of multi-electrode, long, linear-lesion ablation catheters within them, is best accomplished by delivering RF energy to a tip electrode to produce localized spot lesions or if longer lesions are required, by energizing the tip while it is moved across the tissue.

Other catheters for producing spot lesions or tip-drag lesions typically comprise a tip ablation electrode and a plurality of mapping band electrodes positioned at the distal end of the catheter. The catheters are steerable in that they are configured to allow the profile of the distal end of the catheter to be manipulated from a location outside the patient's body. Steerable catheters that produce multiple deflection profiles of their distal ends provide a broader range of steerability. However, known steerable catheters such as that disclosed in U.S. Pat. No. 5,195,968 have steering tendons attached to a ribbon, at or near the longitudinal centerline of the catheter. Because of the relatively short distance between the tendon attachment point and the ribbon that resides along the centerline of the catheter sheath, a force applied to the tendon results in a relatively small bending moment for deflecting the distal tip. The ribbon/tendon assembly is typically provided clearance to allow the tendon to become substantially displaced from the centerline as deflection progresses, thereby enlarging the moment arm and consequently increasing the applied bending moment. Unfortunately, this requires such designs to include additional lumen space, translating into larger catheter diameters. Larger diameter catheters are undesirable due to the increased trauma they inflict on a patient. Further, as the tendon displaces to the extent that it contacts the catheter wall, the associated friction may necessitate greater exertion to further deflect the distal tip. Lessening the amount of force required to deflect the distal tip of a catheter by actions outside the catheter is desired in that the catheter tip can more easily be deflected and placed in the correct location within a patient.

Hence, those skilled in the art have identified a need for a tip-electrode, ablation catheter with a steerable distal-end region that is capable of accessing those areas of the heart which are typically inaccessible by multi-electrode ablation catheters. Needs have also been identified for smaller diameter catheters to improve patient comfort and for more easily deflected catheters so that they may be more easily used. The present invention fulfills these needs and others.

SUMMARY OF THE INVENTION

The invention relates generally to catheters, and more particularly to a catheter having a steerable dual-profile distal-end region.

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery or vein to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate electrophysiological ("EP") catheter system.

One such EP catheter system, as disclosed in U.S. Pat. Nos. 6,059,778 and 6,096,036, includes a plurality of spaced apart band electrodes located at the distal end of the catheter and arranged in a linear array. The band electrodes are positioned proximal heart tissue. RF energy is applied through the electrodes to the heart tissue to produce a series of long linear lesions similar to those produced by the Maze procedure. The catheters currently used for this procedure are typically flexible at the distal end, and the profile at the distal end is adjustable. However, when using such catheters, it is often difficult to conform the distal-end profile to some of the irregular topographies of the interior cavities of the heart. In other instances, it is difficult for a multi-electrode catheter that is designed to produce long linear lesions to access and ablate tissue in regions that require short linear lesions, such as the so-called isthmus region that runs from the tricuspid annulus to the eustachian ridge. Ablation of tissue in this region, and other regions non-conducive to the placement of multi-electrode, long, linear-lesion ablation catheters within them, is best accomplished by delivering RF energy to a tip electrode to produce localized spot lesions or if longer lesions are required, by energizing the tip while it is moved across the tissue.

Other catheters for producing spot lesions or tip-drag lesions typically comprise a tip ablation electrode and a plurality of mapping band electrodes positioned at the distal end of the catheter. The catheters are steerable in that they are configured to allow the profile of the distal end of the catheter to be manipulated from a location outside the patient's body. Steerable catheters that produce multiple deflection profiles of their distal ends provide a broader range of steerability. However, known steerable catheters such as that disclosed in U.S. Pat. No. 5,195,968 have steering tendons attached to a ribbon, at or near the longitudinal centerline of the catheter. Because of the relatively short distance between the tendon attachment point and the ribbon that resides along the centerline of the catheter sheath, a force applied to the tendon results in a relatively small bending moment for deflecting the distal tip. The ribbon/tendon assembly is typically provided clearance to allow the tendon to become substantially displaced from the centerline as deflection progresses, thereby enlarging the moment arm and consequently increasing the applied bending moment. Unfortunately, this requires such designs to include additional lumen space, translating into larger catheter diameters. Larger diameter catheters are undesirable due to the increased trauma they inflict on a patient. Further, as the tendon displaces to the extent that it contacts the catheter wall, the associated friction may necessitate greater exertion to further deflect the distal tip. Lessening the amount of force required to deflect the distal tip of a catheter by actions outside the catheter is desired in that the catheter tip can more easily be deflected and placed in the correct location within a patient.

Hence, those skilled in the art have identified a need for a tip-electrode, ablation catheter with a steerable distal-end region that is capable of accessing those areas of the heart which are typically inaccessible by multi-electrode ablation catheters. Needs have also been identified for smaller diameter catheters to improve patient comfort and for more easily deflected catheters so that they may be more easily used. The present invention fulfills these needs and others.

DETAILED DESCRIPTION OF THE PREFERRED EMBODIMENTS

Figure 1:
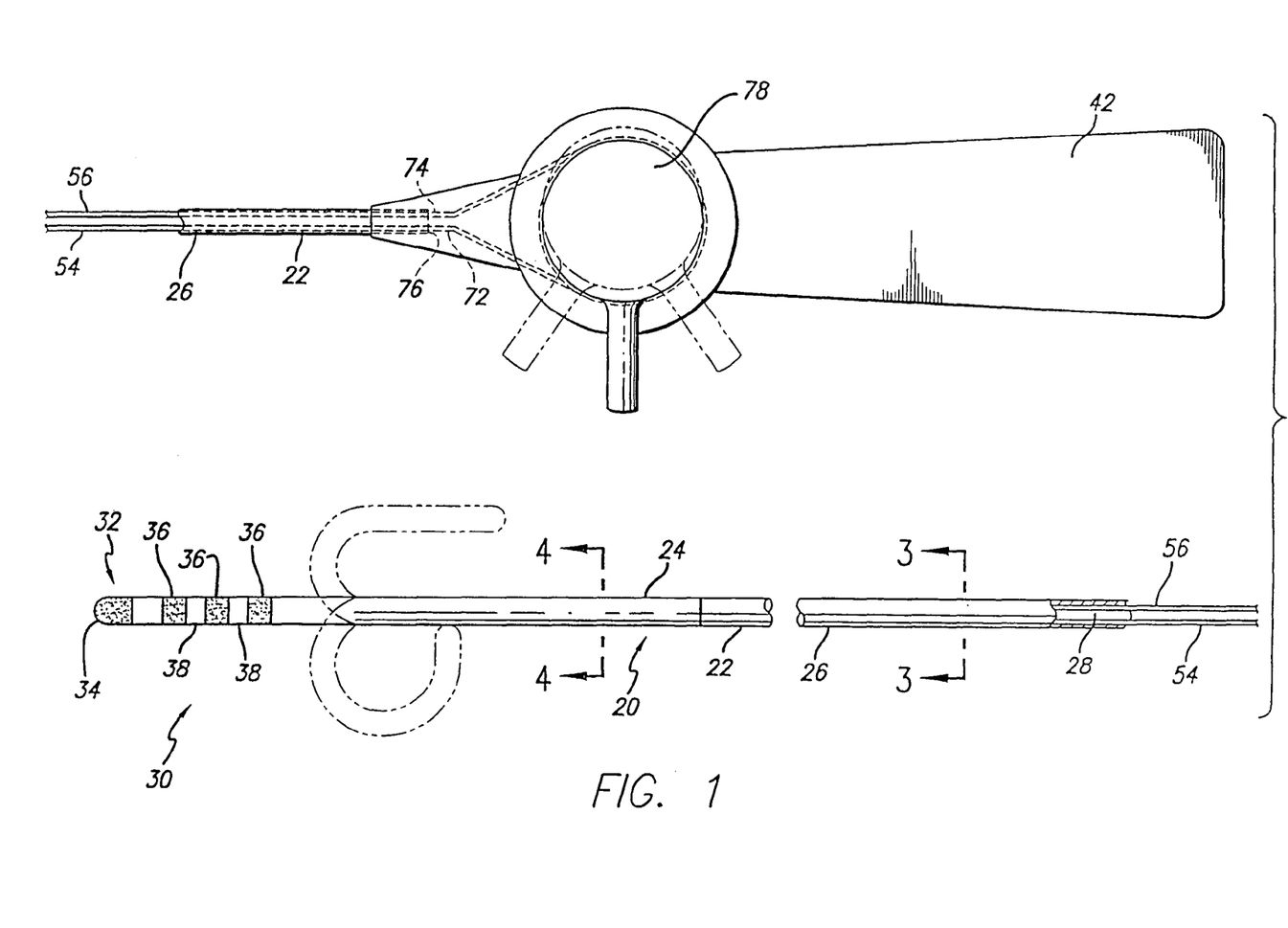
FIG. 1 is a plan view with a broken-out section of a catheter configured in accordance with aspects of the invention and depicting components of the catheter including a sheath, a steering mechanism and a steering handle.

Referring now to the drawings, in which like reference numerals are used to designate like or corresponding elements among the several figures, in FIG. 1 there is shown a catheter 20 incorporating aspects of the present invention. The catheter 20 includes a sheath 22 having a flexible distal-end region 24, a proximal region 26 and an open lumen 28 running throughout. At the distal end 30 of the distal-end region 24 is a distal tip 32. The distal-end region 24 includes a tip electrode 34 for applying ablation energy to a biological site. Located proximal from the tip electrode 34 are three band electrodes 36 arranged in a substantially linear array along the distal-end region 24 of the sheath 22. The band electrodes 36 are arranged so that there is space 38 between adjacent electrodes. In one configuration, the band electrodes 36 are two mm wide and the space 38 between the electrodes is also two mm wide. Alternatively, the band electrodes 36 may be three mm wide and the space 38 between the electrodes may be four mm wide, or other dimensions suitable for mapping and/or ablation procedures. The band electrodes 36 may be used to map the interior surfaces of the heart or to apply ablation energy, or both. The tip electrode 34 may be used to deliver RF energy to the biological site to form spot or tip-drag lesions, or for mapping, or for both.

Figure 2:
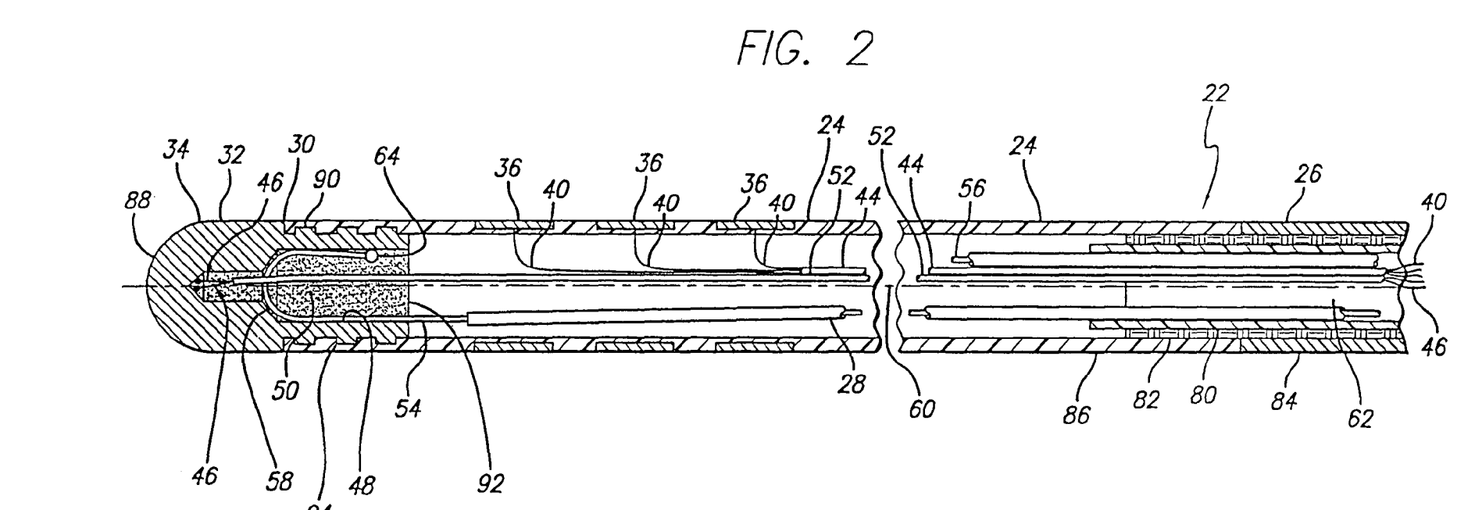
FIG. 2 is a cross-sectional plan view with a broken-out section of the distal portion of the catheter of FIG. 1 depicting detailed components including steering tendons arranged to provide bidirectional steering profile capabilities.

Individual lead wires 40 (not shown in FIG. 1) run from the handle 42 to each band electrode 36. With reference to FIG. 2, the lead wires 40 are attached to the band electrodes 36 in a way that establishes good electrical contact, such as by welding. The lead wires 40 are grouped together and enclosed within a sheath 44 that spans the distal-end region 24 proximal the most proximal band electrode 36 and continues into the proximal region 26 of the sheath 22. The sheath 44 is formed of a flexible material, such as a thin-walled heat-shrink tubing, so that it may deflect when needed.

With further reference to FIG. 2, a pair of thermocouple wires 46 run from the handle 42 shown in FIG. 1 through the sheath 22 to a bore 48 within the tip electrode 34. Each of the thermocouple wires 46 is individually attached at the distal end of the bore 48 in the tip electrode 34 in a way that achieves good electrical contact, such as by soldering. By attaching the thermocouple wires 46 to the tip electrode 34 in this manner, the thermocouple effect is achieved through the tip electrode, and good thermal contact is achieved for a more accurate determination of the temperature of the tip electrode. After being attached to the bore 48, the thermocouple wires 46 are potted into the bore with a resin 50, such as epoxy. One of the thermocouple wires 46 also serves as a drive wire to transmit ablation energy to the tip electrode 34. Exemplary configurations of electrodes having combination thermocouple/drive wires are disclosed in U.S. Pat. Nos. 6,049,737 and 6,045,550. The thermocouple wires 46 are grouped together and enclosed within a sheath 52 that spans throughout the distal-end region 24 and continues into the proximal region 26 of the sheath 22. The sheath 52 is formed of a flexible material, such as a thin-walled heat-shrink tubing, so that it may deflect when needed. In an alternate embodiment, the thermocouple wires 46 are twisted and soldered together prior to being soldered into the tip electrode 34. While the thermocouple effect in this configuration does not depend on the tip electrode 34, the attachment of the thermocouple to the tip electrode does provide the wire pair 46 with good thermal contact.

With continued reference to FIG. 2, housed within the sheath 22 is a first steering tendon 54 and a second steering tendon 56. The distal end 58 of the first steering tendon 54 is offset from a longitudinal centerline 60 of the sheath 22. In order to apply deflection force directly to the distal tip, the distal end 58 of the first steering tendon 54 is inserted into the bore 48 of the distal tip 32. The distal end 58 is then bonded into place with the resin 50. As will be discussed below in more detail, by placing the distal end 58 of the first steering tendon 54 at a location offset from the longitudinal centerline 60 and therefore proximate the inner surface 62 of the sheath 22, a relatively low amount of force applied to the first steering tendon 54 will generate a bending moment sufficient to deflect the distal-end region 24. To ensure a good bond between the resin 50 and the first steering tendon 54 and good anchoring of the tendon within the tip electrode, the distal end 58 of the first steering tendon is hook-shaped with a ball 64 disposed at the end. As will be discussed below in more detail, in one embodiment the distal end 66 (see FIG. 5) of the second steering tendon 56 is attached to the interior surface wall 68 of an anchor band 70 positioned within the distal-end region 24, which places the second steering tendon proximate the inner surface 62 of the sheath 22. With reference to FIG. 1, the proximal end 72 of the first steering tendon 54 and the proximal end 74 of the second steering tendon 56 exit through the proximal end 76 of the sheath 22, and attach to a steering controller 78 within the handle 42.

Figure 3:
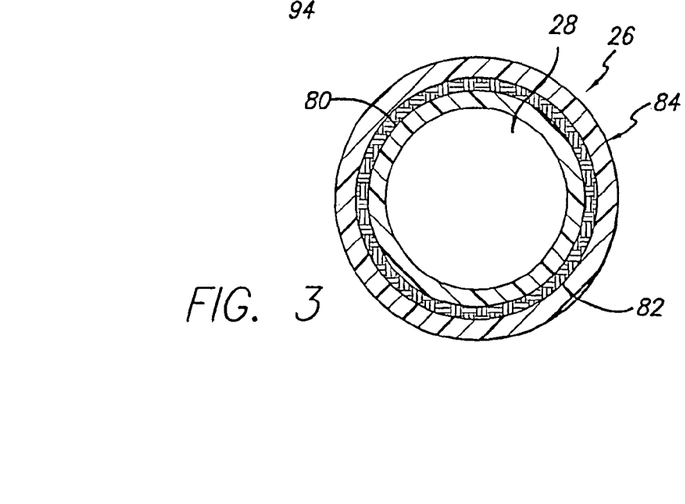
FIG. 3 is a cross-section view of the construction of the proximal region of the sheath taken along the line 3—3 from FIG. 1.

With reference to FIG. 3, which is a cross-sectional view taken from FIG. 1, the proximal region 26 of the sheath 22 is a layered composite. The inner layer 80 is a hollow tube made of a polymer possessing a high modulus of elasticity, such as polyetheretherketone (PEEK). A middle layer 82 having one or more layers of braided, 0.025 mm×0.075 mm stainless steel ribbons is applied upon the inner layer 80 to increase the torque transfer strength of the proximal region 26. Only one layer is shown in FIG. 3 for clarity of illustration. The proximal region's 26 outer layer 84 is made of a flexible, intermediate-durometer polymer such as polyether block amide, known commercially as Pebax™. In one embodiment, the outer layer 84 includes a 63D (shore "D" hardness value) hardness scale Pebax™ tube. The three layers 80, 82, and 84 are bonded together by the simultaneous application of heat and pressure, thus creating a flexible tube with the braided stainless steel ribbons of the middle layer 82 providing superior torsional rigidity. The distal ends of the three layers 80, 82 and 84 are stepped, thus exposing the outer surface of the inner layer and the braided stainless steel ribbons of the middle layer.

Figure 4:
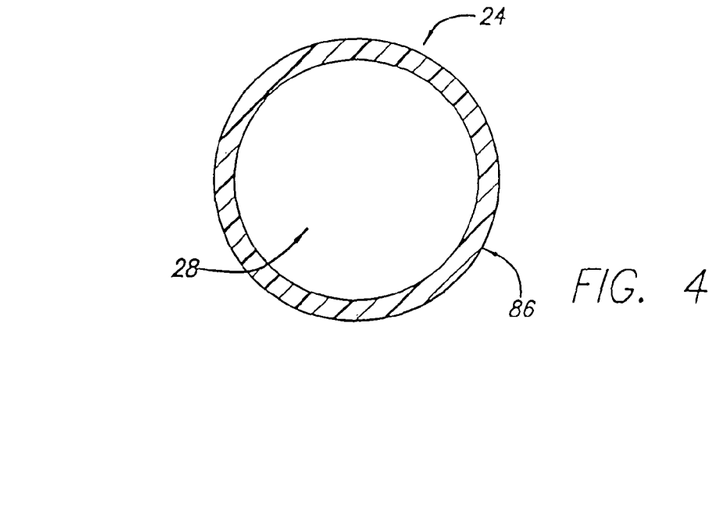
FIG. 4 is a cross-section view of the construction of the distal-end region of the sheath taken along the line 4—4 from FIG. 1.

With reference to FIG. 4, which is a cross-sectional view taken from FIG. 1, the construction of the distal-end region 24 comprises a single layer 86 of a lower durometer Pebax™. In one embodiment, the layer 86 comprises a 35D hardness scale Pebax™ tube. Accordingly, the distal-end region 24 is more flexible than the proximal region 26. To further increase flexibility, the distal-end region 24 of the sheath 22 may have a lower durometer material or a thinner wall.

Referring again to FIG. 2, a proximal portion of the distal-end region 24 of the sheath 22 overlaps the exposed portion of the middle layer 82 of the proximal region 26 and butts against the distal end of the outer layer 84 of the proximal region. The proximal portion of the distal-end region 24 is then bonded to the distal portion of the proximal region 26 to form one continuous sheath 22 through techniques that are well known to those skilled in the art, such as with epoxy. The proximal end 76 of the sheath 22 is bonded to the handle 42 (FIG. 1), such as with cyanoacrylate adhesive, or attached by some equivalent mechanical means.

With further reference to FIG. 2, the tip electrode 34 includes a substantially dome-shaped distal portion 88 and a substantially cylindrical proximal portion 90. The two portions 88, 90 are contiguous and are preferably formed as a single unitary structure. As previously mentioned, the tip electrode 34 includes the bore 48 for receiving the thermocouple/drive wires 46 and first steering tendon 54. The bore 48 penetrates the proximal surface 92 of the proximal portion 90. The proximal portion 90 also includes raised ridges 94 to aid in anchoring the tip electrode 34 to the sheath 22. The tip electrode 34 is formed from a biocompatible material having high thermal conductivity properties. Possible materials include silver, gold, chromium, aluminum, molybdenum, tungsten, nickel, platinum, and platinum/10% iridium.

Figure 5:
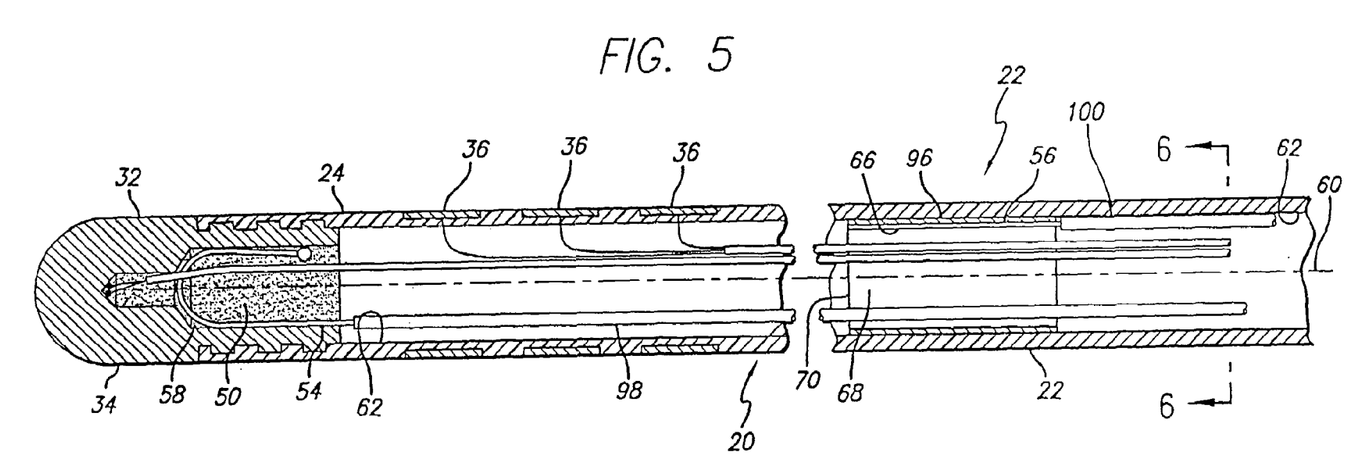
FIG. 5 is a cross-sectional plan view of the distal-end region of the catheter of FIG. 1 depicting the attachment points for the steering tendons, wherein the steering tendons are disposed approximately 180° apart.

With reference to FIG. 5, the anchor band 70 has an inner surface 68 and an outer surface 96. The outer surface 96 of the anchor band 70 is roughened, for example, by machining or by a micro-blasting process, in order to improve adhesion properties. The anchor band 70 is preferably made from a metallic material, such as stainless steel. In this embodiment, the anchor band 70 is located proximal to the most proximal band electrode 36. The distal end 66 of the second steering tendon 56 is welded, soldered, brazed, adhesively bonded, or otherwise attached to the inner surface 68 of the anchor band 70. Such placement puts the distal end 66 of the second steering tendon 56 at a location offset from the centerline 60 of the sheath 22 and proximate the inner surface 62 of the sheath 22. As will be discussed below in more detail, by placing the distal end 66 of the second steering tendon 56 at a location offset from the centerline 60 and proximate the inner surface 62 of the sheath 22, a relatively low amount of force applied to the second steering tendon 56 will generate a bending moment sufficient to deflect the distal-end region 24. The anchor band 70 is then adhered to the inner surface 62 of the sheath 22 within the distal-end region 24, such as by melt-bonding, adhesives, or some equivalent mechanical means.

Figure 6:
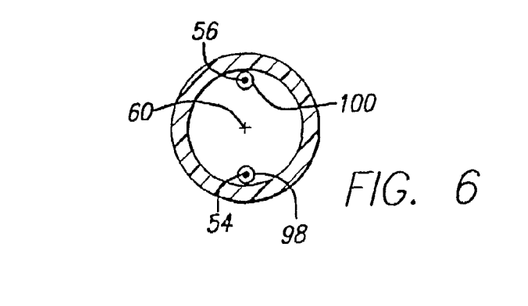
FIG. 6 is a cross-section view of the distal-end region depicting the steering tendons disposed approximately 180° apart, taken along the line 6—6 from FIG. 5.
Figure 7:
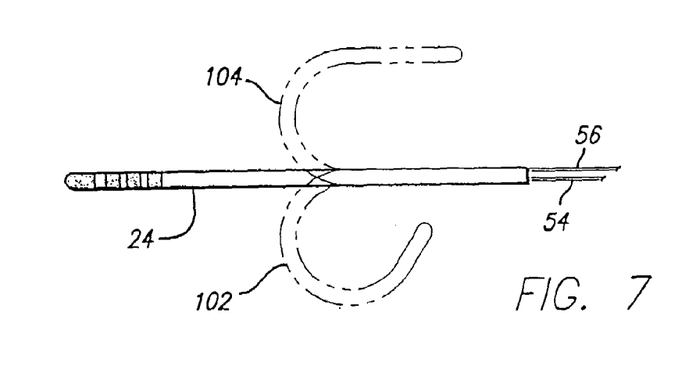
FIG. 7 is a schematic depicting the profiles that may be created within the distal-end region of the catheter of FIG. 5 when the first steering tendon and the second steering tendon are axially displaced in a proximal direction.

With continued reference to FIG. 5, the first steering tendon 54 and the second steering tendon 56 are both housed within the sheath 22, are offset from the centerline 60, and are located proximate the inner surface 62 of the sheath. The first steering tendon 54 is attached at a location distal to the second steering tendon 56. The general orientation of the steering tendons in the present embodiment is shown in the cross-sectional view of FIG. 6 where the first steering tendon 54 is located approximately 180° apart from the second steering tendon 56. As shown in FIG. 7, having the steering tendons 54, 56 attached approximately 180° apart produces deflection profiles of the distal-end region 24 in opposite directions on opposite sides of the catheter 20. In this configuration, the catheter 20 steers in different directions when the steering tendons 54, 56 are axially displaced, thus the catheter is bidirectional.

With further reference to FIG. 5, the steering tendons 54, 56 may be formed from stainless steel wire having a diameter of approximately 0.2 mm. To reduce friction and thereby minimize the force required to steer the catheter 20, the two steering tendons 54, 56 are each enclosed within a respective sheath 98, 100. The sheaths 98, 100 cover substantially the entire length of the steering tendons 54, 56 and provide a relatively small clearance to permit the steering tendons to readily slide within the sheaths 98, 100. The sheaths comprise a tubular, polymeric material and are either coated or are formed of a low friction material, such as polytetrafluoroethylene (PTFE), known commercially as Teflon™.

For clarification purposes, in following discussions, the term "attachment point" in relation to the distal ends 58, 66 of the steering tendons 54, 56 refers to the distal end of the first steering tendon being secured within the distal tip 32 and the distal end of the second steering tendon being attached to the anchor band 70. The bending moments of the steering tendons increase as the distance between the centerline 60 of the catheter sheath 22 and the attachment points of the steering tendons increase. Therefore, in steerable catheters where the steering tendons are attached close to the centerline of the sheath, a relatively greater amount of force may be required to displace the steering tendons in order to deflect or change the profile of the distal-end region. In comparison, by having the distal ends 58, 66 of the steering tendons 54, 56 located at positions offset from the centerline 60 and proximate the inner surface 62 of the sheath 22, the bending moments of the steering tendons are increased. Thus, a relatively low amount of force is required to displace the steering tendons in order to deflect the distal-end region 24.

Referring again to FIG. 5, the distal end 58 of the first steering tendon 54 is secured to the inner wall 48 of the tip electrode 34 at a point away from the catheter centerline 60 and the distal end 66 of the second steering tendon 56 is secured to the inside surface 68 of an anchor band 70 also at a point away from the catheter centerline 60 and near or proximate the catheter wall 62. Both of the tendons 54, 56 run the length of the catheter 20 substantially parallel to the inner surface 62 of the catheter, away from the catheter centerline 60. Applying tension to the proximal end 72, 74 (FIG. 1) of either tendon 54, 56 results in the application of force along the length of the tendon to its distal end 58, 66 attachment point at the tip electrode 34 (first steering tendon) or anchor band 70 (second steering tendon). A tensile force applied to the tip electrode 88 by the first steering tendon 54 is reacted by compressive forces within the sheath 22. Because the first steering tendon's 54 attachment point within the tip electrode 88 is substantially offset from the centerline 60 of the sheath 22, these opposing tensile and compressive forces create a bending moment that acts upon the tip electrode 88. This bending moment deflects the tip electrode 88 and is reacted by the combined bending stiffness of the sheath 22 and other components inside the sheath. Increasing the tensile force on the first steering tendon 54 increases the deflection of the tip electrode 88, thereby decreasing the radius of curvature throughout the length of the sheath 22. The resulting steered profile 102 (FIG. 7) is essentially a circular arc. Similarly, a tensile force applied to the anchor band 70 by the second steering tendon 56 is reacted by forces within the sheath 22. Because the second steering tendon's 56 attachment point within the anchor band 70 is substantially offset from the centerline 60 of the sheath 22, a bending moment acts upon the anchor band. Because the anchor band 70 is affixed to the sheath 22, this bending moment deflects the sheath and is reacted by the combined bending stiffness of the sheath and other components within the sheath proximal the anchor band 70. Increasing the tensile force on the second steering tendon 56 increases the deflection of the sheath 22, thereby decreasing the radius of curvature over the section of sheath that is proximal the anchor band 70. The resulting steered profile 104 (FIG. 7) is essentially a circular arc with a straight section beyond the anchor band 70.

The profile of the distal-end region 24 can be adjusted by manipulating the steering controller 78 (FIG. 1), which axially displaces either the first steering tendon 54 or the second steering tendon 56 in the proximal direction. Axially displacing a steering tendon in the proximal direction causes the steering tendon to experience greater tension. This tension creates a bending moment at the attachment point of the steering tendon 54, 56. For the first steering tendon 54, the bending moment at the tip electrode 34 is the result of the tensile load provided by the tendon at its attachment point and an offset and opposing compressive load provided by the sheath 22. For the second steering tendon 56, the bending moment at the anchor band 70 is the result of the tensile load provided by the tendon at its attachment point and an offset and opposing compressive load provided by the sheath 22.

Either bending moment causes the sheath 22 to compress on the side in which the steering tendon is positioned. This causes a deflection of the distal-end region 24 at the side of the sheath on which the tendon is located, as shown in FIG. 7. By axially displacing the first steering tendon 54 in the proximal direction, the entire distal-end region 24 bends or deflects into a tight loop 102. This is because the location of the attachment point of the distal end 58 of the first steering tendon 54 is on the distal tip 32. But, by axially displacing the second steering tendon 56 in the proximal direction, the distal-end region 24 bends or deflects into a U-shape 104 between the sheath's 22 proximal region 26 and the anchor band 70, while the portion distal the anchor band does not bend. This is because the location of the attachment point of the distal end 66 of the second steering tendon 56 is within the anchor band 70 which is located proximal to the distal tip 32. The bending or deflection profiles 102, 104 of the catheter are somewhat asymmetric, a result of the axial displacement between the distal end mounting locations of the steering tendons 54, 56. The degree of difference in the deflection profiles depends upon the location of the attachment point of the distal end 66 of the second steering tendon 56 in comparison to the first steering tendon 54. Thus, the steering profiles can be altered by changing the location of the attachment point of the distal end 66 of the second steering tendon 56.

Alternatively, although not shown, the distal ends 58, 66 of the steering tendons 54, 56 may both be attached to the distal tip 32 or to the proximal anchor band 70 such that the points of attachment are 1) axially identical along the length of the sheath and 2) angularly displaced from each other along the circumference of the inner surface of the sheath. Such placement of the steering tendons 54, 56 causes the deflection profiles of the catheter 20 to be identical although they will be angularly displaced from each other. For example, when the distal ends 58, 66 of the steering tendons 54, 56 are attached approximately 180° apart along the inner surface of the sheath as shown in FIG. 6, but are attached such that the distal ends are located at the same axial distance from the steering controller 78, the deflections will be symmetric and occur in opposite directions.

Figure 8:
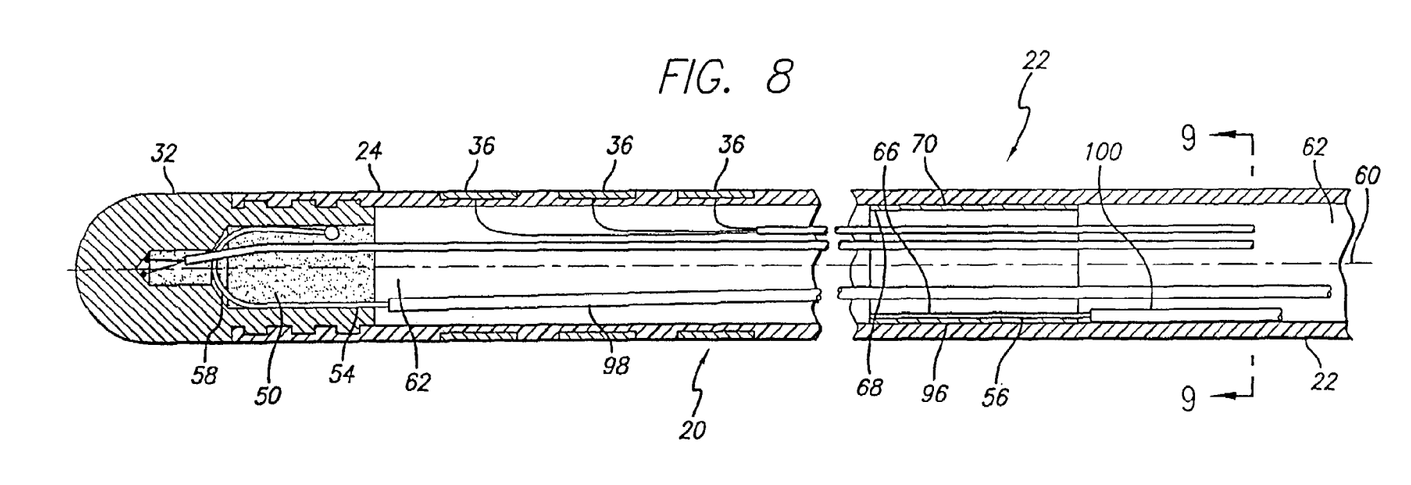
FIG. 8 is a cross-sectional plan view of the distal-end region of another configuration of the catheter of FIG. 1 depicting the attachment points for the steering tendons, wherein the steering tendons are disposed approximately angularly aligned.
Figure 9:
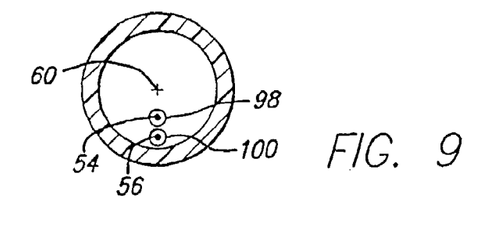
FIG. 9 is a cross-section view of the distal-end region depicting the steering tendons disposed approximately angularly aligned, taken along the line 9—9 from FIG. 8.
Figure 10:
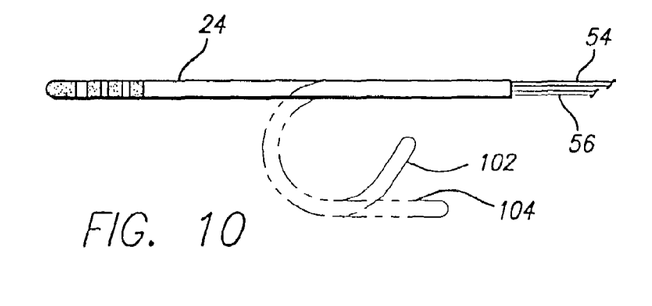
FIG. 10 is a schematic depicting the profiles that may be created within the distal-end region of the catheter of FIG. 8 when the first steering tendon and the second steering tendon are axially displaced in a proximal direction.

With reference to FIG. 8, an alternative embodiment of the catheter of FIG. 1 is depicted wherein both steering tendons 54, 56 are approximately angularly aligned. The first steering tendon 54 is attached at a location distal to that of the second steering tendon 56. The general orientation of the tendons 54, 56 is shown in the cross-sectional view of FIG. 9 where the first steering tendon 54 is located closer to the longitudinal centerline 60 of the catheter sheath 22 than the second steering tendon 56. As shown in FIG. 10, having the steering tendons 54, 56 approximately angularly aligned produces different deflection profiles on the same side of the catheter. In this configuration, the catheter 20 steers in the same direction when either steering tendon 54, 56 is axially displaced, thus the catheter deflection is unidirectional and asymmetric. However, the attachment of the first steering tendon 54 to the catheter sheath 22 at a position distal to the second steering tendon 56 permits a greater curl to the deflected distal end, as shown in FIG. 10. The first dashed profile 102 is achieved through axial movement of the first steering tendon 54 alone while the second dashed profile 104 is achieved through axial movement of the second steering tendon 56 alone.

Although not shown, other attachment configurations are possible. For example, the attachment points for the two steering tendons 54, 56 may be angularly displaced from each other anywhere between approximately 0° to 180° to achieve a different deflection angle for a different location in the patient (FIG. 6 shows 180° angular displacement while FIG. 9 shows 0° angular displacement). In any configuration where the attachment points for the steering tendons 54, 56 are angularly displaced, the catheter 20 steers in different directions when the steering tendons 54, 56 are axially displaced. Therefore, such configurations make the catheter bidirectional, and the two steered profiles may reside either in the same plane or in different planes.

Figure 11:
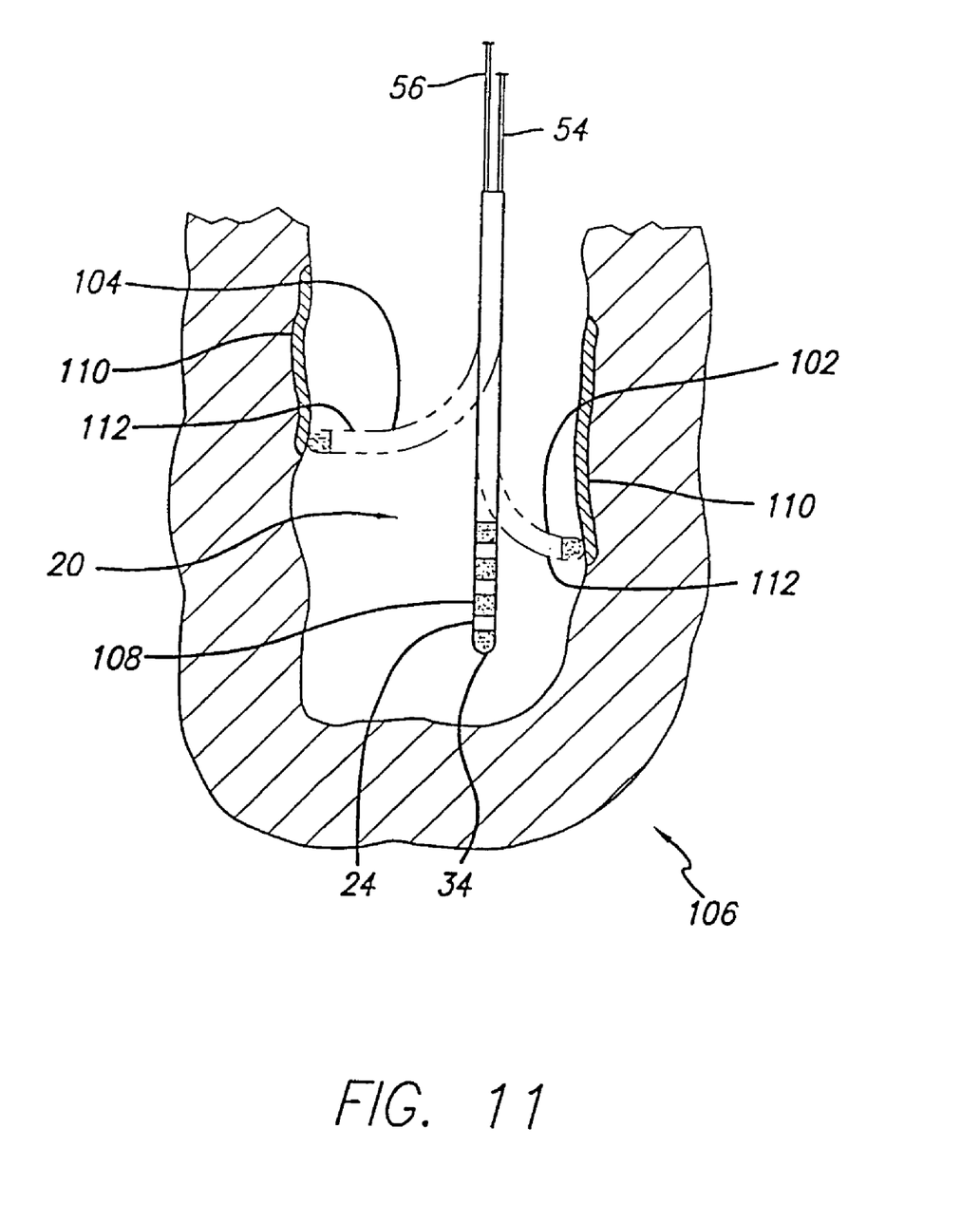
FIG. 11 is a schematic depicting the catheter of FIG. 1 in use in a biological cavity within a patient.

With reference to FIG. 11, in operation, a catheter 20 having bidirectional deflection configured in accordance with the invention is introduced into a biological site 106, such as the right atrium of the heart. During introduction, the catheter 20 is maintained in a substantially linear arrangement 108. While the distal end region 24 of the catheter 20 is being positioned near the area of target tissue 110 to be ablated, the distal-end region is deflected by pulling on the appropriate one of the steering tendons 54, 56, as previously described. Once the distal-end region 24 is adequately deflected 112 to establish contact between the tip electrode 34 and the area of target tissue 110, ablation energy is applied through the tip electrode. If the target tissue 110 comprises a linear segment, the catheter 20 is pulled in the proximal direction during the application of ablation energy to produce a lesion having length, as opposed to only a spot lesion.

Because the location of the attachment point of the first steering tendon 54 to the catheter sheath 22 is more distal than that of the second steering tendon 56 (see FIGS. 5 and 8), for an equal distance of axial translation of the steering tendons the first deflection profile 102 (see FIGS. 7 and 10) does not move the tip electrode 34 as far from the centerline 60 of a non-deflected catheter as does the second deflection profile 104. Also, the first deflection profile 102 may permit more force to be applied to the target site. Therefore, referring to FIG. 11, in instances where the target tissue 110 is located within a compact cavity within the patient, or a relatively higher amount of force is to be applied to the target tissue, it may be desirable to utilize the first deflection profile 102 of the catheter 20. Conversely, where the target tissue 110 is located within a more open cavity within the patient, or a relatively lower amount of force is to be applied to the target tissue, it may be desirable to utilize the second deflection profile 104 of the catheter 20. Hence, because of its ability to be configured with different distal end deflection profiles 102, 104, the catheter 20 of the present invention may be used to form multiple lesions in different environments within a patient without the need of multiple catheters.

It will be apparent from the foregoing that, while particular forms of the invention have been illustrated and described, various modifications can be made without departing from the spirit and scope of the invention.

What is claimed is:

1. A catheter comprising:
a sheath including a proximal region, a distal-end region and a lumen throughout;
a distal tip attached to the distal end of the distal-end region;
a first steering tendon housed within the sheath, the first steering tendon having a first end attached to a first structure at the-distal-end region, and a second end located at the proximal region of the sheath, wherein movement of the first steering tendon in a proximal direction causes the sheath distal-end region to deflect; and
a second steering tendon housed within the sheath, the second steering tendon having a first end attached to a second structure different from the first structure within the lumen of the distal-end region of the sheath at a point proximal to the attachment point of the first end of the first steering tendon, and a second end located at the proximal region of the sheath, wherein movement of the second steering tendon in the proximal direction causes the sheath distal-end region to deflect.

2. The catheter of claim 1, wherein the first steering tendon is secured within the distal tip.

3. The catheter of claim 1, wherein the attachment point of the first steering tendon and the attachment point of the second steering tendon are angularly aligned with each other.

4. The catheter of claim 1, wherein the attachment point of the first steering tendon and the attachment point of the second steering tendon are angularly displaced from each other.

5. The catheter of claim 4, wherein the angular displacement between attachment points is approximately 90°.

6. The catheter of claim 4, wherein the angular displacement between attachment points is approximately 180°.

7. The catheter of claim 1 wherein the first structure comprises a tip electrode, and wherein the first steering tendon is secured within the tip electrode.

8. The catheter of claim 1 wherein the second structure comprises an anchor band attached to an inner surface of the sheath.

9. The catheter of claim 8 wherein the first end of the second steering tendon is attached to an inner surface of the anchor band.

10. The catheter of claim 1 wherein the sheath has a longitudinal centerline, and wherein the first and second steering tendons are offset from the longitudinal centerline.

11. A catheter for use with biological tissue, the catheter comprising:
a sheath including a proximal region, a distal-end region and a lumen throughout;
a distal tip attached to the distal end of the distal-end region;
at least one electrode located in the distal-end region for transferring energy to the biological tissue;
a first steering tendon housed within the sheath, the first steering tendon having a first end attached to a first structure at the distal-end region, and a second end exiting a proximal end of the sheath, wherein movement of the first steering tendon in a proximal direction causes the sheath distal-end region to deflect; and
a second steering tendon housed within the sheath, the second steering tendon having a first end attached to a second structure different from the first structure within the lumen of the distal-end region of the sheath at a point proximal to the attachment point of the first end of the first steering tendon, and a second end exiting the proximal end of the sheath, wherein movement of the second steering tendon in the proximal direction causes the sheath distal-end region to deflect.

12. The catheter of claim 11, wherein the first steering tendon is secured within the distal tip.

13. The catheter of claim 11, wherein the distal tip is a distal tip electrode and the first steering tendon is secured within the distal tip electrode.

14. The catheter of claim 11, wherein the attachment point of the first steering tendon and the attachment point of the second steering tendon are angularly aligned with each other.

15. The catheter of claim 11, wherein the attachment point of the first steering tendon and the attachment point of the second steering tendon are angularly displaced from each other.

16. The catheter of claim 15, wherein the angular displacement between attachment points is approximately 90°.

17. The catheter of claim 15, wherein the angular displacement between attachment points is approximately 180°.

18. The catheter of claim 11 wherein the second structure comprises an anchor band attached to an inner surface of the sheath.

19. The catheter of claim 18 wherein the first end of the second steering tendon is attached to an inner surface of the anchor band.

20. The catheter of claim 11 wherein the sheath has a longitudinal centerline, and wherein the first and second steering tendons are offset from the longitudinal centerline.

* * * * *